United States Patent [19]

Magers et al.

[11] 4,279,993

[45] Jul. 21, 1981

[54] INDICATOR COMPOSITION AND TEST DEVICE CONTAINING AMINE OXIDE, AND METHOD OF USE

[76] Inventors: Thomas A. Magers, 63251 Mulberry Rd., South Bend, Ind. 46614; David L. Tabb, 213 N. Ward St., Elkhart, Ind. 46514

[21] Appl. No.: 93,492

[22] Filed: Nov. 13, 1979

[51] Int. Cl.$^3$ ............................................. C12Q 1/54
[52] U.S. Cl. .................................... 435/14; 23/230 B; 252/408; 422/56; 435/25; 435/28
[58] Field of Search ............... 435/14, 25, 28; 422/56; 23/230 B; 252/408

[56] References Cited

U.S. PATENT DOCUMENTS

| | | | |
|---|---|---|---|
| 4,071,317 | 1/1978 | Lam | 23/230 B X |
| 4,071,321 | 1/1978 | Lam | 23/230 B X |

*Primary Examiner*—Robert J. Warden

[57] ABSTRACT

An improved composition and test device for determining the presence of a constituent in a test sample are disclosed. The composition, which contains a benzidine-type indicator is improved by additionally comprising an amine oxide compound. The device comprises a carrier matrix incorporated with the improved composition. The method comprises contacting the test sample with the composition and observing any detectable response.

45 Claims, No Drawings

INDICATOR COMPOSITION AND TEST DEVICE CONTAINING AMINE OXIDE, AND METHOD OF USE

BACKGROUND OF THE INVENTION

1. Field of the Invention

The present invention relates to the field of analysis of a test sample for the presence of a constituent. More particularly, it relates to a composition capable of producing a detectable response in the presence of the constituent. Such a composition lends itself to the detection of hydrogen peroxide, peroxidase, peroxidatively active substances, various reducing sugars, hypochlorite and other analytes.

The analysis of test samples for the presence of sugars finds utility in many unrelated arts. Thus, the present invention pertains to such diverse arts as the brewing industry, biochemical research and medical diagnostics. In the brewing industry, for example, starch is converted to sugars, such as maltose, prior to actual fermentation. The presence of maltose is therefore carefully monitored to assure high yields from the grain starting material. Many biochemical systems require glucose in carefully controlled concentrations as their cellular energy source, and the research of such systems necessitates that these concentrations be carefully monitored. The medical profession utilizes sugar analysis to a great extent in diagnosing and controlling such diseases as diabetes mellitus, which manifests itself by abnormally high glucose concentrations in the blood and urine.

Likewise many analytical methods are presently available for detecting the presence of peroxidatively active substances in samples such as urine, fecal suspensions, and gastrointestinal contents. Hemoglobin and its derivatives are typical of such "peroxidatively active" substances because they behave in a manner similar to the behavior of the enzyme peroxidase. Such substances are also referred to herein as pseudoperoxidases. Peroxidatively active substances are enzyme-like in that they catalyze the redox reaction between peroxides and benzidine, o-tolidine, 3,3′,5,5′-tetramethylbenzidine, 2,7-diaminofluorene or similar benzidine-type indicator substances, thereby producing a detectable response such as a color change. Most methods for determining the presence of occult blood in test samples rely on this pseudoperoxidase activity.

Thus, the field of the present invention extends to a very diverse assortment of pursuits. It finds applicability wherever sugar analysis becomes a matter of significance, be it in brewing, the food industry, scientific research or medicine. Moreover, it lends itself to a variety of techniques for determining the presence of a peroxidase or pseudoperoxidase. In fact, the present invention finds utility in any field where its unique propensity to exhibit a detectable response is adaptable. Any system which can ultimately provide $H_2O_2$ as a reaction product or which contains peroxidase or a pseudoperoxidase is ripe for application of the present invention, as are other systems such as swimming pool water containing hypochlorite and other strongly oxidizing systems.

2. Description of the Prior Art

The history of sugar analysis is perhaps most noteworthy because it has seen dramatic change over the years, both in the basic chemistries utilized and in its format. For the most part these analyses can be characterized as oxidizing systems which, when reduced, initiate reaction conditions leading to a detectable response, such as a color change or change in wavelength of ultraviolet light absorbed or reflected by the system. Thus, reducing sugars will convert silver oxide to metallic silver, and, if a solution of the sugar is applied to a piece of filter paper impregnated with silver oxide, a black dot develops. F. Feigl, *Chem. Ind.*, Vol. 57, p. 1161, London (1938). Similarly, o-dinitrobenzene and the 3,4- and 3,5-isomers of dinitrophthalic acid give a sensitive color reaction (forming violet shades) when heated with reducing sugars in $Na_2CO_3$. T. Momose, et al., *Chem. Pharm. Bull. Tokyo*, Vol. 12, p. 14 (1964); F. Feigl, *Spot Tests in Organic Analysis*, 7th Edition, pp. 338–339, Elsevier Publ. Co., New York (1966).

But as early as 1849 it was known that reducing sugars would cause an alkaline solution of $CuSO_4$ to precipitate the yellow to red Copper(I)oxide (or oxyhydrate). H. Fehling, *Ann.*, Vol. 72 (1849). See also B. Herstein, *J. Am. Chem. Soc.*, Vol. 32, p 779 (1910). This early milestone, known as the Fehling test, lent impetus to the development of a far more sensitive test which utilized silver oxide in ammonia, the so-called Tollens reagent, which reacts readily with reducing agents to produce a black precipitate of metallic silver, often forming a mirror on the inside walls of glass reaction vessels. B. Tollens, *Ber.*, Vol. 14, p. 1950 (1881); Vol. 15, p. 1635, 1828 (1882).

Because of the relatively high incidence of diabetes mellitus and its accompanying serious clinical consequences, high interest from the biological and medical professions arose in new techniques for analyzing glucose levels in urine and serum. This keen interest led to the development of several procedures which deviate dramatically from their solution chemistry forbears. These utilize sophisticated biochemical systems which can be incorporated into dry, dip-and-read devices, used in solution or suspension techniques, or in conjunction with spectrophotometers and other hardware.

Of these new techniques, the present invention lends itself especially well to an enzymatic system wherein the analyte, for instance glucose, is a substrate for a particular enzyme, the reaction products being capable of eliciting a detectable response from a family of indicator compounds known loosely in the art as "benzidine-type indicators". These will be more carefully defined, infra, but for the present suffice it to say these compounds can undergo color changes in the presence of hydrogen peroxide and the enzyme peroxidase. The glucose/glucose oxidase system exemplifies the prior art, wherein glucose is oxidized to gluconic acid with the concomitant formation of $H_2O_2$ in accordance with:

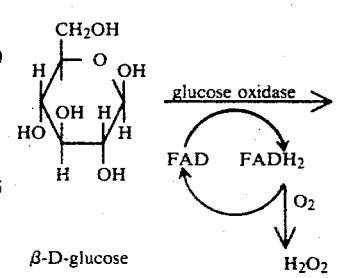

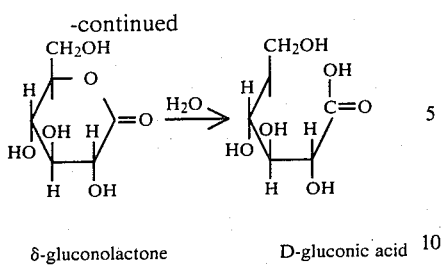

δ-gluconolactone          D-gluconic acid

It is the concomitant formation of hydrogen peroxide which facilitates the subsequent, indicator-related steps leading to observable color formation or other detectable response. Thus a benzidine-type indicator responds in the presence of hydrogen peroxide and peroxidase by changing its light absorptive capability.

In practice, this technology is presently utilized for glucose analysis in the form of dip-and-read reagent strips such as those marketed by the Ames Company Division of Miles Laboratories, Inc. under the trademark CLINISTIX ® and others. Broadly, these comprise a plastic strip, at one end of which is mounted an absorbent paper portion impregnated with the appropriate enzymes, indicator compound and buffering agents as the principal active ingredients. They are used by dipping the reagent-bearing end into the test sample, removing it and comparing any color formed in the paper with a standard color chart calibrated to various glucose concentrations.

Several patents have issued which are deemed pertinent to the present invention with respect to its application to glucose analysis. U.S. Pat. No. 2,848,308, issued to Alfred H. Free, disclosed and claimed the basic enzyme chemistry whereby glucose oxidase, peroxidase and a benzidine-type indicator are used in a reagent strip to determine glucose in urine or other bodily fluid. U.S. Pat. No. 3,753,863, issued to Speck discloses the use of lower alkane polyols to "stabilize" indicator solutions of the benzidine type. Finally, U.S. Pat. No. 4,071,317, issued to Lam, discloses the stabilization of an occult blood-sensitive composition through the use of certain sulfone, sulfoxide and amide compounds as diluents during preparation of the composition. This latter composition comprises an organic hydroperoxide compound, and an indicator compound such as of the benzidine type.

As in the case of sugar analysis, several methods for peroxidase or pseudoperoxidase analysis have evolved over the years which rely on enzymelike catalysis of the oxidation of color-forming indicators in the presence of hydrogen peroxide. Primarily these include wet chemical procedures and "dip-and-read" type reagent-bearing strips. Of the former, a typical example is set forth in Richard M. Henry, et al., *Clinical Chemistry Principles and Techniques* Hagerstown, Maryland: Harper and Row (1974), pp. 1124–1125. This procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity. Inherent to such reagent solutions is a decline in stability (ergo sensitivity) so rapid that fresh reagent solutions must be prepared after several days of storage, a necessity resulting in both excessive time required of analytical personnel, and poor economy because of having to waste costly reagents.

A second method for the determination of peroxidatively active substances, and the one presently preferred by most clinical assayists and analysts, utilizes "dip-and-read" reagent strips. Typical of such devices are reagent strips manufactured by the Ames Company Division of Miles Laboratories, Inc. and sold under the name HEMASTIX ®. These comprise, in essence, a porous paper matrix affixed to a plastic strip or handle. The matrix is impregnated with a buffered mixture of an organic hydroperoxide and o-tolidine. Upon immersion in a liquid containing hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semi-quantitative basis, the amount of unknown present in the sample.

The advantages of reagent strips over wet chemistry methods are predominantly twofold: strips are easier to use because neither the preparation of reagents nor the attendant apparatus is required; and greater stability of reagents is afforded, resulting in greater accuracy, sensitivity and economy.

But the inherent advantages of strips over wet chemistry notwithstanding, the characteristics of stability and sensitivity are in need of still further improvement. Whereas these properties in current state-of-the-art strips for determining pseudoperoxidases and sugars are greatly preferred over those of wet chemical methods, there would nevertheless accrue a great advance in the art if such strips could be made even more stable during storage and even more sensitive to their respective analytes.

At least three attempts at improving pseudoperoxidase-sensitive systems are recorded in the prior art. A recitation in *Chemical Abstracts* Volume 85, page 186 (1976) describes a two-dip method for preparing occult blood-sensitive reagent strips containing o-tolidine and phenylisopropyl hydroperoxide. In this method, a solution was made of the indicator (o-tolidine.2HCl) and polyvinylpyrrolidone in ethanol. To this solution was added a small amount of surfactant and enough citrate buffer to provide a pH of 3.7. Filter paper strips impregnated with ethyl cellulose were dipped in this solution and dried. The thus-impregnated filter paper was subsequently dipped into a second solution containing 1,4-diazabicyclo[2.2.2]octane, phenylisopropyl hydroperoxide and polyvinylpyrrolidone dissolved in an ethanol-toluene mixture. The thrust of this experiment was to stabilize the peroxide and indicator combination through the use of the bicyclooctane derivative and the polyvinylpyrrolidone.

A second such method is disclosed in U.S. Pat. No. 3,853,471. This patent teaches the use of phosphoric or phosphonic acid amides where the substituent amido groups are primarily N-morpholine radicals.

Besides these attempts, there also exists the disclosure of U.S. Pat. No. 3,252,762 wherein the organic hydroperoxide is physically encapsulated within a colloidal material such as gelatin. Thus, when such a test strip is utilized, the aqueous test sample dissolves the gelatin capsules, thereby freeing the hydroperoxide for further reaction with the indicator in the presence of a peroxidatively active substance.

Each of these prior attempts was aimed at stabilizing the reagents so that the potentially incompatible reactive ingredients (hydroperoxide and indicator) would not prematurely combine and thereby render the test strips less sensitive. Hence, it can be said that the prior art methods were not directed towards the combined objectives of simultaneously enhancing stability and sensitivity, but rather they attempted to preserve existing sensitivity by preventing reagent decomposition during storage.

Another prior art reference which is of interest to the general concepts discussed herein is U.S. Pat. No. 3,236,850. This patent is directed towards stabilizing organic hydroperoxides used as catalysts and oxidizing agents. The patentees in this reference disclose the use of primary, secondary, or tertiary amine salts with organic peroxides. This reference is in no way directed toward reagent test strips.

To summarize the state of the art prior to the present invention, sugar-sensitive chemistries began to appear on the analytical scene as early as the middle of the 19th century with the advent of Fehling's solution and Tollens' reagent. Most of the "purely chemical" systems which have since emerged have been largely superseded by biochemical systems, particularly those which comprise a sugar oxidase, peroxidase and a peroxide-sensitive indicator of the benzidine type. These latter indicator compounds have been said to be stabilized by the presence of lower alkyl polyols.

Pseudoperoxidase-sensitive chemistries were also utilized early on as wet chemistry techniques, having given way to dip-and-read techniques involving an organic peroxide and an indicator, such as a benzidine derivative, impregnated in a carrier matrix. Attempts at stabilizing these reagents have included (a) the concomitant use of bicyclooctane and polyvinylpyrrolidone, (b) phosphoric or phosphonic acid amides, (c) physical separation of reagents using gelatin capsules, and (d) primary, secondary and tertiary amine salts.

Finally, a composition sensitive to the presence of occult blood in urine is taught to be stabilized if formulated in the presence of certain sulfone, sulfoxide and/or amide compounds. There is no teaching, to applicants' knowledge, anywhere in the prior art suggesting the presently disclosed and claimed composition and test device, or method for their use.

SUMMARY OF THE INVENTION

Briefly stated, the present invention relates to an improved composition, test device and method for use in detecting the presence of a constituent in a test sample. The composition is capable of producing a detectable response, such as a color change, in the presence of the constituent; and comprises a benzidine-type indicator and, as an enhancer, an amine oxide compound.

The present invention also contemplates a test device comprising a carrier matrix incorporated with the composition. The presence of the particular constituent is determined by contacting the test sample with the device or composition, and observing any detectable response.

DETAILED DESCRIPTION OF THE INVENTION

The present invention is a ramification of the well-known "benzidine-type indicator" system. Benzidine and its derivatives have long been used as chromogenic indicators in assays for such diverse test sample constituents as hypochlorite ion in swimming pool water, and glucose or occult blood in urine. Their ability to develop easily recognizable blue hues of varying intensities renders them capable of both qualitative and semi-quantitative utility. Since the present invention pertains to this indicator system on a broad scale, it is deemed important to elucidate the types of compounds included within the scope of the term "benzidine-type indicator", as well as many currently known systems with which such indicators have been found to be efficacious.

Benzidine and its derivatives ("benzidine-type indicators") are best defined in terms of the structure

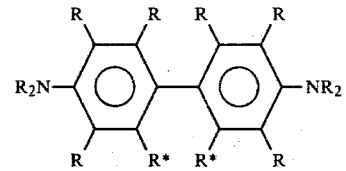

in which the R and R* substituents, same or different, can be hydrogen, lower alkyl (i.e., alkyl having 1 to about 6 carbon atoms), lower alkyloxy (i.e., alkyloxy having 1 to about 6 carbon atoms), aryl or aryloxy. Moreover, the R* substituents can together form $-(CH_2)_n-$ in which n is 1 or 2. In addition to the above characterizations of R and R*, it is understood that these groups, themselves, can be substituted such as with hydroxy, halogen, cyano, etc. Typical compounds embraced by the term "benzidine-type indicator" include benzidine, o-tolidine, o-dianisidine, 3,3',5,5'-tetramethylbenzidine (hereafter "tetramethylbenzidine"), 3,3',5,5'-tetra(alkyl)benzidine, the various N and N'-substitued benzidines and others.

Although the mechanism of color formation from benzidine-type and other indicators in the presence of certain analytes is not known to a certainty, it is known that two sequentially occurring colorforms result: a first species which is blue in color, and a second which is brown. Because the blue species tends to be transient, ultimately metamorphosing to the brown, it is necessary to look for the color change within a prescribed time period. Otherwise the true significance of color change is lost, as subtle shades of blue—which are easily distinguishable—give way to the less easily interpreted brown hues. The higher the analyte concentration in the test sample, the more aggravated this problem becomes due to the limiting effect on capacity to detect the higher ranges of analyte concentrations. Thus, it can be seen that it is highly advantageous to extend the duration of the blue species, thereby permitting greater differentiation between concentrations, as well as providing higher and lower limits to the detectable concentration ranges.

Moreover, because analytical tools such as reagent strips are not used immediately after manufacture, but are usually stored for relatively long periods, and because too long a period between manufacture and use can result in a loss in efficacy leading to false negative results, enhanced shelf life can be a marked asset: the better the shelf life, the more dependable the analytical results.

In addition to the benzidine-type indicator itself, the invention contemplates a myriad of reagent systems which, in the presence of a particular analyte, promote the detectable indicator response, such as a color appearance or change. Thus, if the present composition were to be employed for hypochlorite determination, the indicator and amine oxide composition could be employed by itself, no further reagents being necessary except, perhaps, a buffer.

For the determination of glucose in urine, on the other hand, it is necessary to employ a reagent system comprising, in addition to the present composition, glucose oxidase, peroxidase and a suitable buffer. When such a system is contacted with a urine sample containing glucose, the glucose oxidase catalyzes the oxidation of glucose, yielding $H_2O_2$ as a by-product. In the presence of peroxidase, the $H_2O_2$ causes a color change or appearance in the benzidine-type indicator/amine oxide composition. The purpose of the buffer, if included, is to optimize these reactions by providing the most advantageous pH.

The determination of occult blood or other pseudoperoxidase, or of peroxidase, requires still another reagent system: an organic hydroperoxide, such as cumene hydroperoxide, and, preferably, a suitable buffer. Thus, if pseudoperoxidase is present in the test sample, the organic peroxide/pseudoperoxidase system will interact with the composition of the present invention to yield a color change enabling qualitative and semi-quantitative pseudoperoxidase analysis.

The enhancer compound of the present invention, an amine oxide, has been found to promote sensitivity by permitting an observable color appearance at analyte levels lower than those possible with identical systems without the enhancer present. The enhancer permits analyte to be semi-quantitatively assessed at much higher concentrations as well. Thus, the entire range of analyte concentrations detectable with a particular reagent system and benzidine-type indicator is expanded when the enhancer of the present invention is present in the formulation.

The amine oxides contemplated as being within the scope of the invention cover a broad range. They have the structure $$R'_3N \rightarrow O$$

wherein the R' substituents, same or different, can be hydrogen, lower alkyl, lower alkyloxy, aryl, or aryloxy. By "lower alkyl" is meant a hydrocarbon radical having from 1 to about 6 carbon atoms, including methyl, ethyl, n-propyl, isopropyl, n-butyl, isobutyl, tert-butyl, cyclobutyl and all the various isomers of pentyl and hexyl. The term "lower alkyloxy" is similarly defined, being ethers of lower alkyl radicals. These substituents can themselves be substituted, such as with hydroxy, halogen, cyano and others. In addition, two R' substituents and the nitrogen atom to which they are bound can together form a closed ring having 3 to about 6 atoms. The ring can be saturated, unsaturated or aromatic. Moreover, it can be substituted, such as by hydroxyl, halogen and alkyl.

Moreover, the ring can itself be one of many pendant groups in a polymeric molecule. Examples of the latter are poly(4-vinylpyridine-1-oxide) and poly(2-vinylpyridine-1-oxide). These can be represented, respectively, by the structural formulas

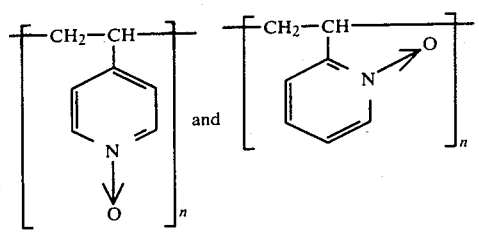

wherein the bracketed structure represents the amine oxide monomer unit and n is the relative number of monomer units in an average polymer chain, the value of n being dictated by the degree of polymerization.

In addition to these polymers, other amine oxides which are included within the scope of this invention are trimethylamine oxide, tri-($\beta$-hydroxyethyl)amine oxide, i.e., triethanolamine oxide, pyridine-1-oxide, 3-hydroxypyridine-1-oxide, 4-methylpyridine-1-oxide, and 2-chloropyridine-1-oxide and 4,4'-azobis(pyridine-1-oxide). Especially useful as enhancers are 3-hydroxy- and 2-chloropyridine-1-oxides.

The amount of amine oxide used in conjunction with the benzidine-type indicator is not critical, although an amount in the range of about 50 to 800 or more mole percent based on the moles of indicator has been found to be effective in achieving the aforementioned enhanced indicator sensitivity. Using this basis as a guideline, although not necessarily requisite, the amounts of the present composition to be used with the various chemistries for the desired analytes can be easily determined from the prior art, as well as from the Examples provided below.

The test device of the present invention comprises a carrier matrix incorporated with the indicator/amine oxide composition. Moreover, it can be additionally incorporated with any art-recognized or other reagent system useable with a benzidine-type indicator, such as the glucose- and pseudo-peroxidase-sensitive systems discussed above.

The carrier matrix utilized in forming the test device can take on a multitude of forms. Thus, U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take on various physical forms. All of these types are intended as being within the scope of the present invention.

Whichever is chosen, a web of carrier matrix material can be incorporated with the present composition in several ways. The web can be drawn through a solution or suspension of the indicator and amine oxide in an appropriate solvent such as water, methanol, benzene, cyclohexane, etc. After drying, the composition-laden matrix web can then be slit into strips about 0.5 cm. wide and fastened to one edge of a strip of plastic backing material measuring about 8 cm. in width. This can be achieved using a double-faced adhesive tape known as Double Stick available from the 3M Company. The backing material with the matrix strip in place is then cut widthwise to form reagent strips measuring 8×0.5 cm. having a 0.5 cm. square of reagent laden carrier matrix at one end, the other end serving as a handle.

Another way of incorporating a carrier matrix with the present composition is by printing. U.S. Pat. No. 4,046,513 describes such a technique whereby an ink comprising the composition is silk screened onto a plastic carrier matrix. Still other ways, such as spraying the composition onto the matrix, are part of the prior art, and thus would be within the ken of a person or ordinary skill in the art.

The following Examples are provided to further illustrate the composition and test device of the present invention, as well as the method for their use. Included are the embodiments of these three facets of the invention presently considered preferred, and which are presently deemed to be the best mode of performance of the invention. Moreover, as can be seen from the foregoing discussion, the presently disclosed concepts are very broad in scope; and the succeeding Examples should not be deemed as being in any way limiting.

EXAMPLES I–VIII

Glucose Detection

A series of experiments was performed in order to assess the efficacy of the presently claimed composition in determining the presence of glucose in aqueous solution. A basic solution of glucose oxidase, peroxidase and o-tolidine was prepared. To seven aliquots were added seven different amine oxides; an eighth aliquot containing no amine oxide served as a control. A sample of each solution was tested with gradually increasing amounts of glucose to determine (a) initial blue color formation as well as (b) the onset of browning.

The basic reagent solution contained the following ingredients:

| | | |
|---|---|---|
| o-tolidine | 0.25 | grams (g) |
| poly(vinylpyrrolidone) (10% by weight in water) | 30.0 | milliliters (ml) |
| ON 870 polyethoxylated fatty alcohol (General Aniline & Film Corp.) | 0.25 | g |
| ethanol (denatured with 5 ml methanol per 100 ml solution) | 18.0 | ml |
| buffer* | 23.5 | ml |
| Gantrez AN-139 obtained from G.A.F. Corp. (10% by weight of maleic anhydride vinyl ether copolymer in water) | 7.5 | ml |
| ascorbic acid (10% by weight in water) | 0.25 | ml |
| glucose oxidase in water (5000 I.U. per ml available from the Marschall Division of Miles Laboratories, Inc.) | 7.5 | ml |
| horseradish peroxidase (68 I.U. per miligram, available from Miles Laboratories, Inc.) | 0.25 | g |
| water | 13.25 | ml |
| *A mixture consisting of: | | |
| water | 208.0 | ml |
| tris-hydroxymethylaminomethane (Fisher Scientific) | 22.5 | g |
| trisodium citrate | 27.2 | g |
| glutamic acid | 27.0 | g |
| citric acid | 6.16 | g |

The resulting mixture was divided into eight aliquots of 19 ml each, and 0.1 g of a different amine oxide (see Table I) was added to seven of the aliquots, the eighth serving as a control. 1.0 ml portions of each aliquot were placed in separate wells of a spot plate. To each was added 1 μl (microliter) of aqueous glucose solution (1% by weight). The onset of blue color was timed and qualitatively characterized. Following this, more of the glucose solution was added until brown coloration was detected, and the amount of glucose solution noted. Glucose addition was performed using a calibrated syringe (Hamilton Series No. 700, 10 μl capacity). The initial 1 μl quantity was added instantaneously. No more glucose was added until a blue color formed and its time noted, whereupon the additional glucose was added. In each case the additional glucose was added within 60 seconds.

TABLE I

| Example | Amine Oxide | Initial Blue Color Formation (1 μl glucose) | Glucose Required Before Browning Occurred |
|---|---|---|---|
| I | (control) | blue ring formed after 60 seconds (sec.) | 20 μl |
| II | 4-methylpyridine-1-oxide | entire surface blue - 7 sec. | 35 μl |
| III | 3-hydroxypyridine-1-oxide | entire surface blue - 7 sec. | 42 μl |
| IV | 2-chloropyridine-1-oxide | blue ring - 5 sec. | 45 μl |
| V | trimethylamine oxide | entire surface blue - 5 sec. | 28 μl |
| VI | poly(4-vinylpyridine-1-oxide) | entire surface blue - instantaneous | 35 μl |
| VII | poly(2-vinylpyridine-1-oxide) | entire surface blue - instantaneous | 28 μl |
| VIII | 4,4'-azobis(pyridine-1-oxide) | entire surface blue - 5 sec. | 25 μl |

The data from Examples I–V show that the four amine oxides studied improved the basic glucose reagent by (a) dramatically reducing the time required for blue color formation at low glucose levels, and (b) forestalled the appearance of the brown colorform of the indicator until much greater concentrations of glucose were reached. Thus, it can be said that the presence of an amine oxide in the glucose formulation permits a dramatic extension or broadening of the range of glucose concentrations detectable using the current state-of-the-art enzyme chemistry.

EXAMPLES IX AND X

Detection of a pseudoperoxidase

A solution was prepared containing, as active ingredients, o-tolidine, glucose oxidase, and buffer. Two 19 ml aliquots of this system were set aside for testing. To one aliquot was added 0.1 grams of trimethylamine oxide; the other aliquot served as a control. Each solution was then tested by adding a small amount of hemoglobin followed by a small amount of glucose. The presence of hemoglobin was indicated by the formation of blue color. In theory the glucose oxidase acts on the glucose to form hydrogen peroxide. The peroxide interacts with o-tolidine in the presence of a pseudoperoxidase (here, hemoglobin) to produce a blue color.

The initial solution was prepared by combining the following ingredients:

| | |
|---|---|
| o-tolidine | 0.1 g |
| buffer* | 4.7 ml |
| ethanol | 3.6 ml |
| poly(vinylpyrrolidone) (10% by weight in water) | 6.0 ml |
| Gantrez AN-139 (10% by weight of maleic anhydride/vinyl ether copolymer in water) | 1.5 ml |
| glucose oxidase in water (5000 I.U. per ml) | 1.5 ml |

Two aliquots of 19 ml. of this mixture were set aside and to one aliquot was added 0.1 grams of trimethylamine oxide. A 19 ml portion of each aliquot was placed in a separate well of a spot plate. To each of these was added 1 μl of an aqueous hemoglobin solution, assayed at 160 red blood cells per ml., and 5 μl of an aqueous solution of glucose (10 grams glucose per liter of water). The results are reported in Table II.

TABLE II

| Example | Amine Oxide | Observed Results |
|---|---|---|
| IX | (control) | barely discernible response after 60 sec. |
| X | trimethylamine oxide | a definite blue ring formed around the edge of the spot plate well within 30 sec. |

The results of this comparative experiment demonstrate the enhanced sensitivity of the amine oxide-containing mixture in detecting very small amounts of pseudoperoxidase such as hemoglobin. Whereas, under the experimental conditions of Example IX a blue color formation was barely discernible even after 60 seconds, the same system under the same experimental conditions yielded a definite blue ring around the well of the spot plate after only 30 seconds when a small amount of an amine oxide was present.

What is claimed is:

1. In a composition for detecting the presence of a constituent in a test sample wherein said composition comprises a benzidine-type indicator having the structure

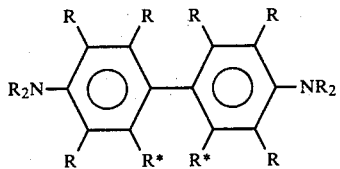

in which the R and R* substituents, same or different, are hydrogen, lower alkyl, lower alkyloxy, aryl, or aryloxy, or in which the R* substituents together comprise $-(CH_2)-_n$ in which n is 1 or 2, the improvement wherein said composition additionally comprises, as an enhancer, an amine oxide compound.

2. The improved composition of claim 1 wherein said amine oxide is trimethylamine oxide, triethanolamine oxide, pyridine-1-oxide, 3-hydroxypyridine-1-oxide, 4-methylpyridine-1-oxide, 2-chloropyridine-1-oxide, poly(4-vinylpyridine-1-oxide), poly(2-vinylpyridine-1-oxide) or 4,4'-azobis(pyridine-1-oxide).

3. The improved composition of claim 1 wherein said amine oxide is 2-chloropyridine-1-oxide.

4. The improved composition of claim 1 wherein said amine oxide is 3-hydroxypyridine-1-oxide.

5. The improved composition of any of claims 1-3 or 4 wherein said indicator is benzidine.

6. The improved composition of claim 5 which additionally comprises glucose oxidase and peroxidase.

7. The improved composition of claim 5 which additionally comprises an organic hydroperoxide.

8. The improved composition of any of claims 1-3 or 4 wherein said indicator is o-tolidine.

9. The improved composition of claim 8 which additionally comprises glucose oxidase and peroxidase.

10. The improved composition of claim 8 which additionally comprises an organic hydroperoxide.

11. The improved composition of any of claims 1-3 or 4 wherein said indicator is 3,3',5,5'-tetramethylbenzidine.

12. The improved composition of claim 11 which additionally comprises glucose oxidase and peroxidase.

13. The improved composition of claim 11 which additionally comprises an organic hydroperoxide.

14. The improved composition of any of claims 1-3 or 4 which additionally comprises glucose oxidase and peroxidase.

15. The improved composition of any of claims 1-3 or 4 which additionally comprises an organic hydroperoxide.

16. In a test device for detecting the presence of a constituent in a test sample wherein said device comprises a carrier matrix incorporated with a composition which comprises a benzidine-type indicator having the structure

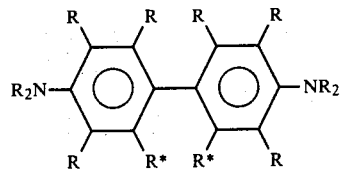

in which the R and R* substituents, same or different, are hydrogen, lower alkyl, lower alkyloxy, aryl, or aryloxy, or in which the R* substituents together comprise $-(CH_2)-_n$ in which n is 1 or 2, the improvement wherein said composition additionally comprises, as an enhancer, an amine oxide compound.

17. The improved test device of claim 16 wherein said amine oxide is trimethylamine oxide, triethanolamine oxide, pyridine-1-oxide, 3-hydroxypyridine-1-oxide, 4-methylpyridine-1-oxide, 2-chloropyridine-1-oxide, poly(4-vinylpyridine-1-oxide), poly(2-vinylpyridine-1-oxide) or 4,4'-azobis(pyridine-1-oxide).

18. The compound test device of claim 16 wherein said amine oxide is 2-chloropyridine-1-oxide.

19. The improved test device of claim 16 wherein said amine oxide is 3-hydroxypyridine-1-oxide.

20. The improved test device of any of claims 16-18 or 19 wherein said indicator is benzidine.

21. The improved test device of claim 20 which additionally comprises glucose oxidase and peroxidase.

22. The improved test device of claim 20 which additionally comprises an organic hydroperoxide.

23. The improved test device of any of claims 16–18 or 19 wherein said indicator is o-tolidine.

24. The improved test device of claim 23 which additionally comprises glucose oxidase and peroxidase.

25. The improved test device of claim 23 which additionally comprises an organic hydroperoxide.

26. The improved test device of any of claims 16–18 or 19 wherein said indicator is 3,3',5,5'-tetramethylbenzidine.

27. The improved test device of claim 26 which additionally comprises glucose oxidase and peroxidase.

28. The improved test device of claim 26 which additionally comprises an organic hydroperoxide.

29. The improved test device of any of claims 16–18 or 19 which additionally comprises glucose oxidase and peroxidase.

30. The improved test device of any of claims 16–18 or 19 which additionally comprises an organic hydroperoxide.

31. A method for determining the presence of a constituent in a test sample, said method comprising the steps of contacting the sample with a composition which comprises a benzidene-type indicator having the structure

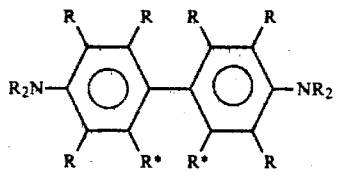

in which the R and R* substituents, same or different, are hydrogen, lower alkyl, lower alkoxy, aryl, or aryloxy, or in which the R* substituents together comprise $-(CH_2)_n-$ in which n is 1 or 2, and an amine oxide compound, and observing any detectable response.

32. The method of claim 31 wherein said amine oxide is trimethylamine oxide, triethanolamine oxide, pyridine-1-oxide, 3-hydroxypyridine-1-oxide, 4-methylpyridine-1-oxide, 2-chloropyridine-1-oxide, poly(4-vinylpyridine-1-oxide), poly(2-vinylpyridine-1-oxide) or 4,4'-azobis(pyridine-1-oxide).

33. The method of claim 31 wherein said amine oxide is 2-chloropyridine-1-oxide.

34. The method of claim 31 wherein said amine oxide is 3-hydroxypridine-1-oxide.

35. The method of any of claims 31–33 or 34 wherein said indicator is benzidine.

36. The method of claim 35 wherein said composition additionally comprises glucose oxidase and peroxidase.

37. The method of claim 35 wherein said composition addtionally comprises an organic hydroperoxide.

38. The method of any of claims 31–33 or 34 wherein said indicator is o-tolidine.

39. The method of claim 38 wherein said composition additionally comprises glucose oxidase and peroxidase.

40. The method of claim 38 wherein said composition additionally comprises an organic hydroperoxide.

41. The method of any of claims 31–33 or 34 wherein said indicator is 3,3',5,5' tetramethylbenzidine.

42. The method of claim 41 wherein said composition additionally comprises glucose oxidase and peroxidase.

43. The method of claim 41 wherein said composition additionally comprises an organic hydroperoxide.

44. The method of any of claims 31–33 or 34 wherein said composition additionally comprises glucose oxidase and peroxidase.

45. The method of any of claims 31–33 or 34 wherein said composition additionally comprises an organic hydroperoxide.

* * * * *

UNITED STATES PATENT AND TRADEMARK OFFICE
CERTIFICATE OF CORRECTION

PATENT NO. : 4,279,993
DATED : July 21, 1981
INVENTOR(S) : Thomas Anthony Magers & David Lee Tabb It is certified that error appears in the above-identified patent and that said Letters Patent are hereby corrected as shown below:

Page 1, Column 1, after the paragraph "[76] Inventors: ...", insert --- [73] Assignee: Miles Laboratories, Inc., Elkhart IN ---

Page 1, Column 2 beneath "*Primary Examiner* - Robert J. Warden", insert --- *Attorney, Agent or Firm* - Edward H. Gorman, Jr. ---.

Signed and Sealed this

Third Day of November 1981

[SEAL]

Attest:

Attesting Officer

GERALD J. MOSSINGHOFF

Commissioner of Patents and Trademarks